(12) United States Patent
Gaughan et al.

(10) Patent No.: US 10,139,387 B2
(45) Date of Patent: Nov. 27, 2018

(54) QUARTZ CRYSTAL CHARACTERIZATION OF FRACTIONS DERIVED FROM CRACKED STREAMS

(71) Applicant: ExxonMobil Research and Engineering Company, Annandale, NJ (US)

(72) Inventors: Roger Grant Gaughan, Biltmore Lake, NC (US); David John Abdallah, Moorestown, NJ (US); Dennis Harold Hoskin, Westampton, NJ (US); Manuel S. Alvarez, Warrenton, VA (US); Christopher J. Wolfe, Fort McMurray (CA)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 63 days.

(21) Appl. No.: 14/818,623

(22) Filed: Aug. 5, 2015

(65) Prior Publication Data

US 2016/0047788 A1    Feb. 18, 2016

Related U.S. Application Data

(60) Provisional application No. 62/036,713, filed on Aug. 13, 2014, provisional application No. 62/036,909, filed on Aug. 13, 2014.

(51) Int. Cl.
*G01N 29/036* (2006.01)
*G01N 33/22* (2006.01)
(Continued)

(52) U.S. Cl.
CPC ........... *G01N 33/22* (2013.01); *G01N 29/022* (2013.01); *G01N 29/036* (2013.01);
(Continued)

(58) Field of Classification Search
CPC ............................ G01N 29/036; G01N 33/22
(Continued)

(56) References Cited

U.S. PATENT DOCUMENTS 4,808,538 A   2/1989  Roffey et al.
7,253,644 B2  8/2007  Song
(Continued)

OTHER PUBLICATIONS

E.A. Klaavetter, S.J. Martin and K.O. Wessendorf, "Monitoring Jet Fuel Thermal Stability Using a Quartz Crystal Microbalance", Energy & Fuels, 1993, vol. 7, pp. 582-588.
(Continued)

*Primary Examiner* — Hezron E Williams
*Assistant Examiner* — Alex Devito
(74) *Attorney, Agent, or Firm* — Glenn T. Barrett

(57) ABSTRACT

Methods are provided for characterizing the stability of a distillate fraction using a quartz crystal microbalance apparatus, such as a distillate fraction derived at least in part from a pre-refined crude oil. A sample can be aged for an aging period in a quartz crystal microbalance apparatus, and a frequency value for the sample in the quartz crystal microbalance apparatus can be determined before and after the aging period to determine a frequency difference. This frequency difference can be correlated directly with the ability of a jet fuel fraction to satisfy a stability test standard, such as a jet fuel breakpoint stability. The methods can also include using a temperature profile during characterization that can reduce or minimize operator error during the characterization.

20 Claims, 10 Drawing Sheets

(51) Int. Cl.
*G01N 29/02* (2006.01)
*G01N 29/44* (2006.01)

(52) U.S. Cl.
CPC ... *G01N 29/4427* (2013.01); *G01N 2291/014* (2013.01); *G01N 2291/0224* (2013.01); *G01N 2291/0426* (2013.01)

(58) Field of Classification Search
USPC .............................................. 73/64.53, 61.79
See application file for complete search history.

(56) References Cited

U.S. PATENT DOCUMENTS

| | | | |
|---|---|---|---|
| 9,103,813 B2 | 8/2015 | Kusinski et al. | |
| 9,140,679 B2 | 9/2015 | Kusinski et al. | |
| 9,347,009 B2 | 5/2016 | Kusinski et al. | |
| 9,394,497 B2 | 7/2016 | Gaughan et al. | |
| 9,464,242 B2 | 10/2016 | Kusinski et al. | |
| 2015/0192558 A1* | 7/2015 | De Coninck | G01N 29/022 73/61.49 |
| 2015/0323441 A1* | 11/2015 | Lachance | G01N 11/16 73/54.24 |
| 2016/0319208 A1 | 11/2016 | Gaughan et al. | |

OTHER PUBLICATIONS

S. Zabarnick, "Studies for Jet Fuel Thermal Stability and Oxidation Using a Quartz Crystal Microbalance and Pressure Measurements", Industrial Engineering and Chemical Research, 1994, vol. 5, No. 5, pp. 1348-1354.

\* cited by examiner

QUARTZ CRYSTAL CHARACTERIZATION OF FRACTIONS DERIVED FROM CRACKED STREAMS

CROSS REFERENCE TO RELATED APPLICATIONS

This application relates and claims priority to U.S. Provisional Patent Application No. 62/036,713, filed on Aug. 13, 2014, entitled "Quartz Crystal Characterization of Distillate Fractions."

This application also relates to U.S. Provisional Patent Application No. 62/036,709, filed on Aug. 13, 2014, entitled "Quartz Crystal Characterization of Fractions Derived from Pre-Refined Crudes."

FIELD OF THE INVENTION

This invention relates to method for producing and characterizing distillate fractions derived at least in part from cracked fractions.

BACKGROUND OF THE INVENTION

Petroleum fractions used for jet fuel are typically qualified in part by an ASTM standard (ASTM D3241) to verify the suitability (ASTM D1655) of a petroleum fraction for use. Once a fraction is found to meet the specification from ASTM D1655, it is conventionally assumed that a jet fuel fraction and/or a finished blended jet fuel product will remain stable over time and therefore will remain within the specification limits and not need subsequent testing for requalification for use.

One of the difficulties in applying ASTM D3241 and/or D1655 is that these measurements provide a snapshot of the characteristics of a jet fuel fraction and/or finished jet fuel product. By contrast, the specification for stability of a jet fuel fraction corresponds to a stability over the course of time, such as a period of months or possibly a year or greater. Naturally, waiting an extended period of time to perform a characterization test for a jet fuel fraction and/or finished jet fuel product can lead to variety of logistical difficulties in identifying suitable crude fractions for forming jet fuels. In order to overcome some of these difficulties, a characterization method based on accelerated aging was developed and described in pending U.S. application Ser. No. 14/021,028. However, the method described in Ser. No. 14/021,028 still corresponds to a time-consuming method for determining whether a potential jet fuel product is fit for purpose.

Use of quartz crystals as part of a measurement apparatus, such as in a Quartz Crystal Microbalance (QCM) apparatus, has previously been described in various literature references. Although a variety of configurations may be suitable for construction of an apparatus incorporating a quartz crystal, one standard option for constructing a QCM apparatus is described in ASTM D7739.

SUMMARY OF THE INVENTION

In an aspect, a method of characterizing a kerosene boiling range sample is provided. The method includes disposing a quartz crystal in a vessel containing a kerosene boiling range sample; heating the kerosene boiling range sample to a baseline temperature; measuring a frequency of the quartz crystal at the baseline temperature during a first sampling period to obtain a baseline frequency; heating the kerosene boiling range sample to an aging temperature and maintaining the sample at the aging temperature for an aging period; returning the kerosene boiling range sample to the baseline temperature; and measuring the frequency of the quartz crystal at the baseline temperature during a second sampling period to obtain an aged frequency, a difference between the baseline frequency and the aged frequency being indicative of a stability of the kerosene boiling range sample.

In another aspect, a method of characterizing a distillate fraction is provided. The method includes determining a breakpoint for a first sample of a distillate fraction, the distillate fraction having an initial boiling point of at least about 284° F. (140° C.) and a final boiling point of about 572° F. (300° C.) or less, at least a portion of the distillate fraction being derived from a pre-refined crude oil, a cracked fraction, or a combination thereof, the determined breakpoint being greater than about 265° C.; heating a second sample of the distillate fraction in a vessel of a quartz crystal microbalance apparatus to an aging temperature, the aging temperature being from about 40° C. to about 90° C., the quartz crystal microbalance apparatus comprising a quartz crystal, the quartz crystal being disposed in the second sample during the heating; and measuring a baseline frequency and an aged frequency of the quartz crystal, the aged frequency being measured after maintaining the second sample of the distillate fraction at the aging temperature for an aging period, the baseline frequency being measured prior to maintaining the second sample of the distillate fraction at the aging temperature for the aging period, the aging period being from about 5 hours to about 24 hours, wherein a difference between the baseline frequency and the aged frequency is indicative of a stability of the distillate fraction.

In still another aspect, a method of characterizing a distillate boiling range sample is provided. The method includes determining a breakpoint for a first sample of a distillate fraction, the distillate fraction having an initial boiling point of at least about 284° F. (140° C.) and a final boiling point of about 572° F. (300° C.) or less, at least a portion of the distillate fraction being derived from a pre-refined crude oil, a cracked fraction, or a combination thereof, the determined breakpoint being greater than about 265° C.; heating a second sample of the distillate fraction in a vessel of a quartz crystal microbalance apparatus to an aging temperature for an aging period, the quartz crystal microbalance apparatus comprising a quartz crystal, the quartz crystal being disposed in the second sample during the heating; measuring a baseline frequency and an aged frequency of the quartz crystal, the aged frequency being measured after maintaining the second sample of the distillate fraction at the aging temperature for an aging period, the baseline frequency being measured prior to maintaining the second sample of the distillate fraction at the aging temperature for the aging period, a difference between the baseline frequency and the aged frequency for the second sample being greater than or equal to a threshold frequency difference value; hydrotreating or chemical treating a third sample of the distillate fraction under effective treating conditions to form a treated third sample of the distillate fraction; heating at least a portion of the treated third sample of the distillate fraction in a vessel of a quartz crystal microbalance apparatus to the aging temperature for the aging period, the quartz crystal microbalance comprising a quartz crystal, the quartz crystal being disposed in the at least a portion of the treated third sample during the heating; and measuring a baseline frequency and an aged frequency for the at least a portion of the treated third sample of the distillate fraction using a quartz crystal microbalance apparatus, the aged frequency being measured after maintaining the treated third sample of the distillate fraction at the aging temperature for the aging period, a difference between the baseline frequency and the aged frequency for the at least a portion of the treated third sample being less than the threshold frequency difference value. Optionally, the hydrotreating or chemical treating of the third sample under effective treating conditions can comprise hydrotreating the third sample under effective hydrotreating conditions.

In yet another aspect, a method of characterizing a distillate boiling range fraction is provided. The method includes determining a breakpoint for a first sample of a distillate fraction, the distillate fraction having an initial boiling point of at least about 284° F. (140° C.) and a final boiling point of about 572° F. (300° C.) or less, the distillate fraction being derived from a pre-refined crude oil, a cracked fraction, or a combination thereof, the determined breakpoint being greater than about 265° C.; heating a second sample of the distillate fraction in a vessel of a quartz crystal microbalance apparatus to an aging temperature for an aging period, the quartz crystal microbalance apparatus comprising a quartz crystal, the quartz crystal being disposed in the second sample during the heating; measuring a baseline frequency and an aged frequency of the quartz crystal, the aged frequency being measured after maintaining the second sample of the distillate fraction at the aging temperature for an aging period, the baseline frequency being measured prior to maintaining the second sample of the distillate fraction at the aging temperature for the aging period, a difference between the baseline frequency and the aged frequency for the second sample being greater than or equal to a threshold frequency difference value; blending a portion of the distillate fraction derived from the pre-refined crude oil, the cracked feedstock, or the combination thereof with a portion of a mineral distillate fraction to form a blended distillate fraction; and measuring a baseline frequency and an aged frequency for a sample derived from the blended distillate fraction using a quartz crystal microbalance apparatus, the aged frequency being measured after maintaining the sample derived from the blended distillate fraction at the aging temperature fir the aging period, a difference between the baseline frequency and the aged frequency for the sample derived from the blended distillate fraction being less than the threshold frequency difference value.

DETAILED DESCRIPTION OF THE EMBODIMENTS

Overview

Figure 1:
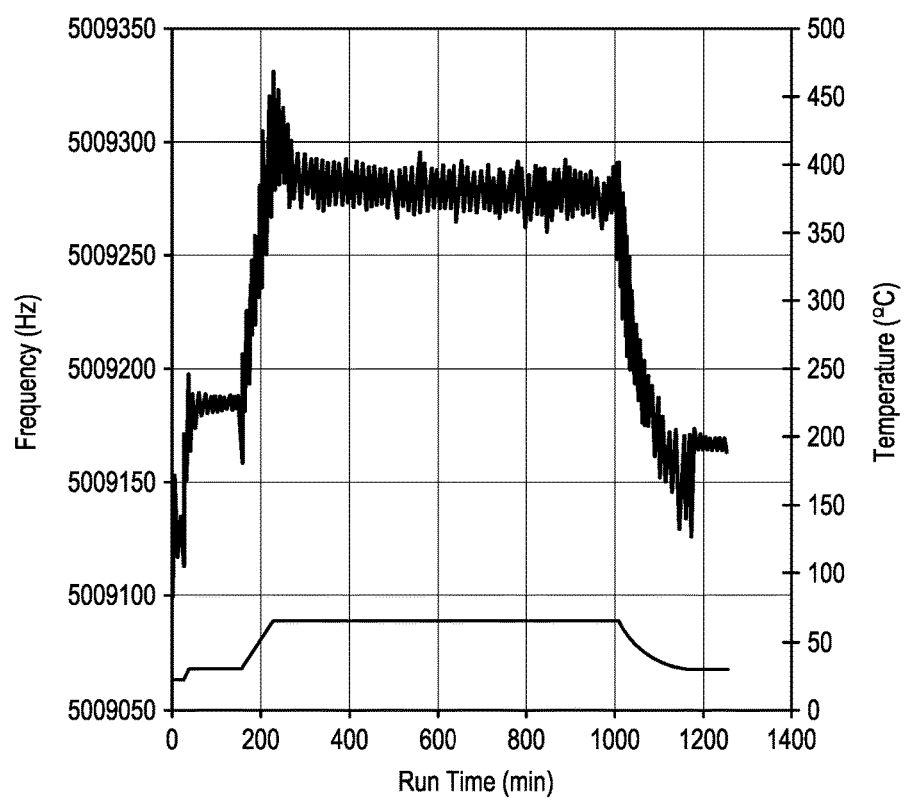
FIG. 1 shows an example of a temperature profile for determining a breakpoint stability (below, right-hand axis) and corresponding frequencies measured using a quartz crystal using the temperature profile (above, left-hand axis).

In various aspects, methods are provided for determining that potential jet fuel fractions and/or finished jet fuel products (such as jet fuel products derived in part from pre-refined crude sources) are fit for use as jet fuel (or "fit for purpose") using a quartz crystal microbalance (QCM) apparatus. The methods allow for determination of the stability of a jet fuel product in a time period on the order of hours as opposed to the weeks or months of time required using conventional methods for determining jet fuel stability. This can be achieved, for example, based on a correlation of a) a frequency shift for a sample that is detected using an apparatus based on a QCM with b) a stability for a potential jet fuel fraction as determined using a longer time frame test. Optionally, a jet fuel fraction and/or finished jet fuel product that is characterized using a QCM apparatus can correspond to a fraction that is derived at least in part from pre-refined crude oil sources. Optionally, a jet fuel fraction and/or finished jet fuel product that is characterized using a QCM apparatus can correspond to a cracked fraction that is derived at least in part from the effluent of a cracking process.

In some aspects, a method for determining the stability of a jet fuel fraction or finished product using a QCM apparatus includes using a temperature profile during characterization that can reduce or minimize operator error during the characterization. For example, a sample placed in a QCM apparatus can be heated to a first temperature greater than room temperature to establish a baseline frequency at the first temperature. The sample can then be heated to a second temperature to "age" or accelerate reactions of lower stability components within the sample. The temperature of the sample can then be returned to the first temperature to observe the difference in frequency relative to the initial baseline frequency. This frequency difference can be correlated directly with the ability of a jet fuel fraction or finished product to satisfy a stability test standard, such as a jet fuel breakpoint stability. Thus, if the difference between the baseline frequency and the final frequency is less than a threshold value, the sample can be considered sufficiently stable to be fit for purpose in a jet fuel product. Similarly, if the frequency difference is greater than the threshold value, the sample can be considered as not sufficiently stable for use in a finished jet fuel product.

Conventional Stability Testing for Jet Fuel Products

Jet fuel products (and/or fractions for incorporation into such products) are generally tested using breakpoint procedure that is defined in ASTM D3241. The test involves flowing a sample in an elevated temperature environment over a metal heater tube under specified conditions. For example, a jet fuel product sample (and/or fraction for incorporation into a jet fuel product) can be passed from a reservoir over a metal heater tube at a desired temperature, such as 260° C., and at a pressure of about 500 psig (3.44 MPag). The output from the metal heater tube is then passed through a differential pressure filter. The flow rate from the reservoir is typically maintained at a constant value, such as 3.0 ml/min for a set period of time, such as 150 minutes. After the test, the deposits on the metal heater tube are evaluated by metrology where the deposit film thickness is measured as described in ASTM 3241 (e.g., visual tube rating) for color. This establishes a "tube rating" for the test. The maximum pressure drop across the filter is also determined. A sample is deemed to pass the test if both the tube rating (or film thickness) and pressure drop values are satisfactory.

One option is to test a sample at a single temperature, such as 260° C., to qualify the sample for use. Another option is to determine a breakpoint for the sample. To identify a breakpoint, a series of tests are performed at temperatures that differ by an interval of 5° C. At lower temperatures, the sample for the potential jet fuel product (or fraction for incorporation into a product) will pass the tube rating or film thickness (deposits) and pressure drop tests. As the temperature is increased, a temperature interval will eventually be reached where the sample has satisfactory tube rating and pressure drop values at the temperature on the lower side of the interval while failing one or both of the tube rating and pressure drop portions of the test on the high temperature side of the interval. The lower temperature of the pair of temperatures corresponding to the interval is defined as the breakpoint for the sample. In other words, the breakpoint temperature is a temperature where any further temperature increase is likely to result in failure of the sample to pass the test defined in ASTM D3241.

The method for determining a breakpoint temperature can be expanded to provide a method for determining the stability of a sample, such as a mineral kerosene sample, a sample containing at least a portion that is derived from an effluent from a cracking process (i.e., a cracked fraction), and/or a sample containing at least a portion that is derived from a pre-refined crude. First, a breakpoint temperature can be determined for a sample of a fraction and/or product that is potentially suitable as a jet fuel product and/or potentially suitable for incorporation into a jet fuel product. A portion of the fraction or product (possibly a portion of the same initial sample) is then aged for a period of time under conditions that are designed to simulate a desired storage period. The breakpoint for the aged portion is then measured again. This stability test provides an indication of the behavior of the sample over time. If the breakpoint for the aged sample is still above the temperature needed for use as a jet fuel, such as a breakpoint of 260° C. or greater, then jet fuel products with a pre-refined crude content equal to or less than the content of the aged sample is potentially suitable for use.

Additionally or alternately, a sample may also be characterized to determine that any breakpoint degradation that occurs during aging of the sample is within an acceptable tolerance. For example, a sample of a potential jet fuel product (and/or fraction for incorporation into a product) can be initially tested to verify that the breakpoint of the sample is at least 270° C. A sample of the potential jet fuel product or fraction can then be aged for a period of time, such as aging for the equivalent of a year. The breakpoint for the aged sample can then be determined. If the differential between the breakpoint of the initial sample and the aged sample is small enough, the sample can be suitable for use in a jet fuel product from a stability standpoint. For example, a breakpoint degradation of less than 10° C. for a sample aged for the equivalent of a year can be deemed suitable for use. For an initial sample with a breakpoint of at least 270° C., a sample with suitable stability after the equivalent of aging for a year will also result in the aged sample having a breakpoint of at least 260° C.

One way to age a jet fuel product sample for stability testing is to store a sample at an elevated temperature, such as a temperature above 40° C. For example, storing a jet fuel product sample at a temperature of 43° C. for a week has been demonstrated to be equivalent to storing the jet fuel product sample at ambient temperature (e.g., 20° C.) for a month (see ASTM D4625). This allows for testing of the breakpoint for a sample before and after an aging period to determine the impact of aging on the properties of the sample. The difference between the breakpoint temperature for a sample before and after aging can be correlated with the stability of a potential jet fuel fraction and/or finished jet fuel product. The amount of difference in breakpoint temperature that can be tolerated is dependent on the length of the aging.

One option for a combination of breakpoint temperature differential and length of aging is to determine whether a sample has a difference in breakpoint temperature of 10° C. or less after the equivalent of a year of aging. Samples with a difference in breakpoint temperature of 10° C. or less can be considered as sufficiently stable for use in a finished jet fuel product, while samples with a greater difference after aging for the equivalent for a year can be identified as not suitable.

For example, a sample with a breakpoint of 275° C. before aging and a breakpoint of at least 265° C. after aging for 12 weeks at 43° C. (aging roughly equivalent to a year) is still suitable for use as a jet fuel, even though the breakpoint for the sample has decreased. In this situation, the breakpoint of the sample has changed by 10° C. or less during the equivalent of aging for 1 year. By contrast, a sample with a breakpoint of 280° C. before aging and a breakpoint of less than 270° C. (such as 260° C. or 265° C.) after aging for 12 weeks at 43° C. may or may not be suitable for use as a jet fuel. In this example, the breakpoint of the aged sample still satisfies the ASTM D3241 breakpoint requirement. However, the degradation of the breakpoint by more than 10° C. during the equivalent of aging for 1 year may indicate a sample that will continue to degrade in an unacceptable manner.

More generally, sample stability can be tested for jet fuel product samples (or fractions having an appropriate boiling range for incorporation into a jet fuel product) by increasing the aging temperature for samples of the potential product. After identifying an initial breakpoint temperature for the jet fuel product (or fraction for incorporation into a product), one or more samples of the jet fuel product can be aged at a temperature above 40° C. for at least 6 weeks, such as for at least 10 weeks or at least 12 weeks. Examples of suitable testing temperatures are 43° C. as described in ASTM D4625, 65° C. as described in CRC report CA-43-98, or 95°

C. as described in ASTM D2274. Preferably, the aging temperature is about 43° C. After aging, the breakpoint for an aged sample is determined again to verify that the sample still passes the tube rating and pressure drop tests at a sufficiently high temperature to qualify for use as a jet fuel product.

In the discussion herein, references to a "breakpoint" are references to a JFTOT™ type breakpoint as defined by ASTM D3241. (JFTOT™ refers to a jet fuel thermal oxidation test defined in ASTM D3241. JFTOT™ is currently a registered to trademark of Petroleum Analyzer Company.) A minimum breakpoint for suitable jet fuel products is defined in ASTM D1655 as 260° C. Such a breakpoint is often determined with regard to a specification, such as the specification provided in ASTM D1655. For a typical sample, characterizing the sample for JFTOT™ at a single temperature can take a few hours, while determining a breakpoint can take several days. References to a "breakpoint stability" are references to a difference in the JFTOT™ breakpoint tier a potential jet fuel product sample (or fraction for incorporation into a product) prior to sample aging and after the sample is aged over a period of time. Using conventional methods, such a stability characterization can take weeks. In various aspects, the methods for using a QCM apparatus as described herein can facilitate evaluation of the breakpoint stability of a various samples in a time frame of hours or days, which is similar to the time required for determining the breakpoint of a sample without aging.

Characterization Using a Quartz Crystal Microbalance Apparatus

One difficulty with the breakpoint stability tests described above is the length of time required for determining a breakpoint stability value. The multiple weeks required for conventional breakpoint stability characterization make breakpoint stability testing difficult to incorporate into a commercial process. One of the benefits of the methods described herein is that a determination of breakpoint stability can be made on a time scale of hours instead of a time scale of weeks.

Figure 8:
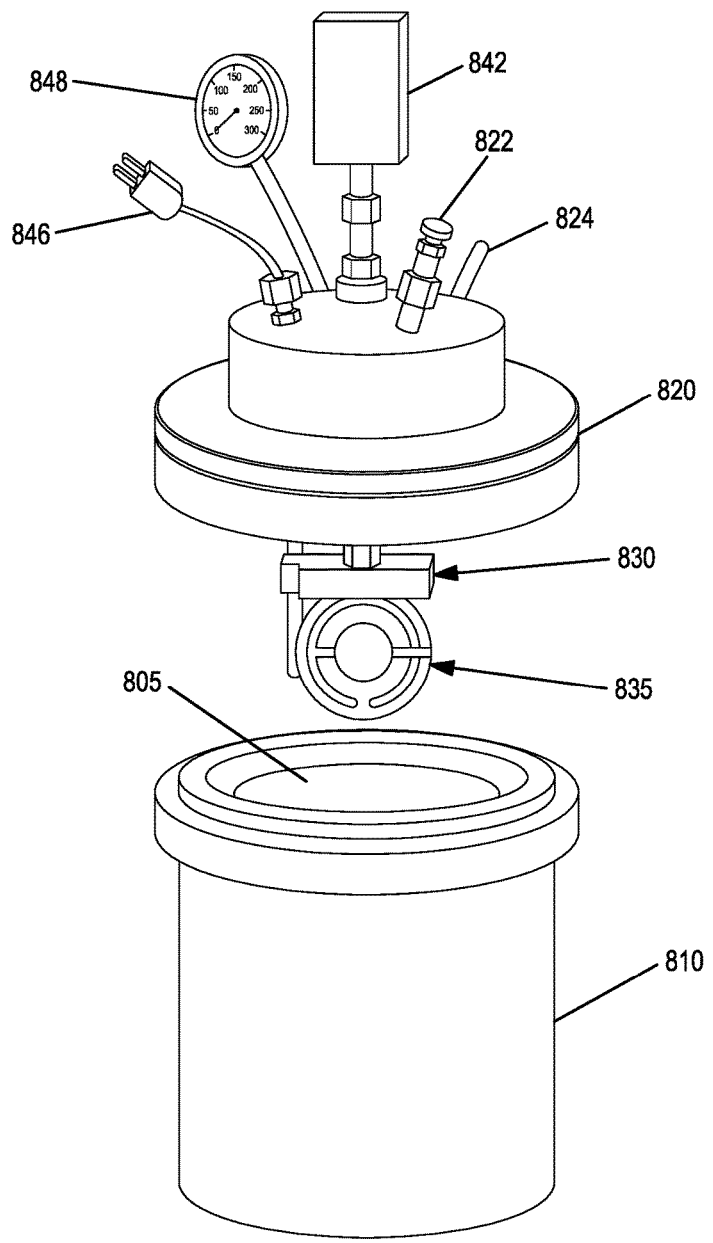
FIG. 8 schematically shows a measurement apparatus incorporating quartz crystals.

Traditionally, one application for using a quartz crystal microbalance apparatus can be to determine an amount of mass that deposits on the quartz crystal during a time period, such as the deposited mass during heating of a sample. FIG. 8 schematically shows an example of an apparatus incorporating a quartz crystal to determine an amount of material that deposits on the quartz crystal. In FIG. 8, the outer shell of the apparatus can include a vessel 810 and a lid or cover 820. The quartz crystal 835 is mounted on lid 820 as part of a protrusion 830 that extends into the vessel when the lid is placed on the vessel. An oscillator 842 for exciting the quartz crystal 835 is also provided. Additionally, the lid can allow for mounting or provision of other features for using the apparatus, such as a vent 822, gas inlet 824, thermocouple 846, and pressure gauge 848.

During operation, a sample 805 to be tested can be placed in vessel 810 (such as a sample of a jet fuel boiling range fraction or finished jet fuel product). The lid 820 is then placed on the vessel 810, which results in quartz crystal 835 being disposed in the sample 805. The oscillator 842 can be used to excite the quartz crystal 835, which allows an initial frequency to be measured. The vessel (or at least the sample inside the vessel) can then be heated to induce potential deposition on the crystal. As material deposits on the crystal, the natural or resonant frequency of the crystal can be changed, and this change in the resonant frequency can be detected.

In a traditional use, the change in frequency of the quartz crystal can be used to determine an amount of mass deposited on the crystal. One option for determining the stability of a sample could be to correlate the mass deposited on the crystal with a sample stability. While such a conversion of frequency to mass could be performed in some aspects, it is not necessary for characterizing the stability of a sample in the methods described herein. Instead, the frequency change itself can be used for characterizing the stability of the sample.

It has been determined that the breakpoint stability of a sample of a potential jet fuel fraction and/or finished product can be correlated with a shift in the resonant frequency of a quartz crystal that is exposed to the sample while the sample is heated using a suitable heating profile. One example of a correlation between the frequency shift of a quartz crystal from a QCM apparatus and a breakpoint stability is that a frequency shift of about 40 Hz or greater in a sample exposed to a suitable heating profile corresponds to a sample that will fail a breakpoint stability test. In other words, a sample that shows a frequency shift of about 40 Hz or greater corresponds to a sample that will exhibit a change in breakpoint of, for example, at least about 11° C. per year under a breakpoint stability test. If the sample has a frequency shift of less than 40 Hz after exposure to the heating profile, the sample corresponds to a sample that will pass a breakpoint stability test corresponding to a 10° C. or less difference in breakpoint after aging for the equivalent of a year. For other stability measurements involving another difference in breakpoint temperature relative to another period of time, another frequency shift might be appropriate. Thus, similar correlations between a frequency difference and a breakpoint stability for a different period of time can be developed.

To characterize a sample using a QCM apparatus, a sample is placed in a vessel of a QCM apparatus, such as a QCM apparatus constructed according to ASTM D7739. An initial frequency measurement can be performed on the sample to determine a frequency for the quartz crystal after placing the crystal in the sample within the vessel. After obtaining the initial frequency measurement, the temperature of the sample is increased to a higher temperature for a time period, such as between about 5 hours and about 24 hours, or between about 8 hours and about 20 hours. During the aging period at a higher (aging) temperature, the exposure of the sample to the aging temperature can cause reaction and/or degradation of the sample. Without being bound by any particular theory, it is believed that the reactions and/or degradation of the sample can result in deposition of material on the quartz crystal disposed within the vessel holding the sample, leading to changes in the natural resonant frequency of the quartz crystal. This change in resonant frequency can be measured to determine whether the sample will have sufficient stability. The change in frequency can be detected at the elevated temperature, or the frequency difference can be detected after returning the sample to the temperature of the initial frequency measurement.

The elevated temperature used for characterizing the stability of the sample can be any convenient temperature between about 40° C. to about 100° C. For example, the temperature can be increased to at least about 45° C., or at least about 50° C. or at least about 60° C. Additionally or alternately, the temperature can be increased to about 90° C. or less, or about 80° C. or less, or about 70° C. or less. Each of the above upper and lower temperature bounds is explicitly contemplated in combination with one another. Thus, explicitly contemplated temperature ranges include, but are not limited to, about 45° C. to about 100° C., or about 45° C. to about 90° C., or about 45° C. to about 80° C., or about 50° C. to about 100° C., or about 50° C. to about 90° C., or about 60° C. to about 100° C., or about 60° C. to about 90° C., or about 50° C. to about 80° C., or about 60° C. to about 80° C. Lower temperatures can prevent unnecessary degradation of stable samples that might lead to false positives in characterization, but can also increase the amount of time required for characterizing a sample. Higher temperatures can lead to general degradation of a sample, so that temperatures above 100° C. are not suitable for correlating a change in a quartz crystal frequency with a breakpoint stability measurement.

FIG. 1 shows an example of heating a sample in a QCM apparatus in order to determine a frequency shift for the quartz crystal disposed in the sample, which then allows determination of a breakpoint stability for the sample. In FIG. 1, the upper curve corresponds to frequency measurements deft-side axis) for the quartz crystal disposed in the sample, while the lower curve shows the temperature profile (right-side axis) fir the sample during the frequency measurements. As shown in FIG. 1, an initial frequency measurement is made for a sample in a QCM apparatus at ambient temperature. In the example shown in FIG. 1, the temperature is then increased to about 60° C. and held at that temperature for about 16 hours. This leads to an initial increase in the frequency, and then a slow drop in frequency over the course of the 16 hours. The temperature is then reduced to ambient, leading to a drop in the measured frequency. The frequency measurements shown in FIG. 1 can then be used to determine a frequency shift either at the elevated temperature (60° C.) or at the initial temperature (ambient). It is noted that the sample characterized in FIG. 1 corresponds to a sample containing about 47 wt % of components corresponding to pre-refined crude sources. The measured frequency shift in FIG. 1 is about 18 Hz, indicating that the sample in characterized in FIG. 1 has sufficient breakpoint stability to be suitable for use as and/or incorporation into a finished jet fuel product.

Figure 7:
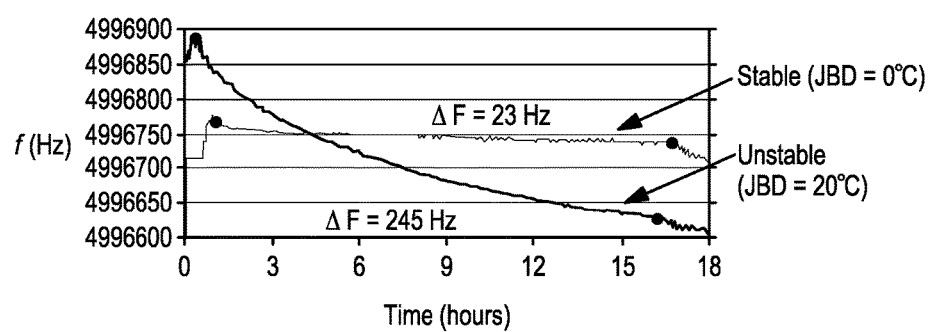
FIG. 7 shows the difference in frequency change measured in a quartz crystal microbalance apparatus for a sample that can satisfy a breakpoint stability test (frequency change of 23 Hz) and for a sample that cannot satisfy a breakpoint stability test (frequency change of 245 Hz).

More generally, FIG. 7 shows a correlation between a) the frequency shift of a quartz crystal for samples characterized using a QCM apparatus with an appropriate heating profile and b) the breakpoint stability of the samples. As shown in FIG. 7, for a sample that can satisfy a breakpoint stability test, the frequency shift over time for the sample remains small even though the sample is exposed to elevated temperatures. By contrast, a sample that cannot satisfy the breakpoint stability test shows a frequency shift of greater than 40 Hz after being exposed to a suitable temperature profile in a QCM apparatus.

Figure 2:
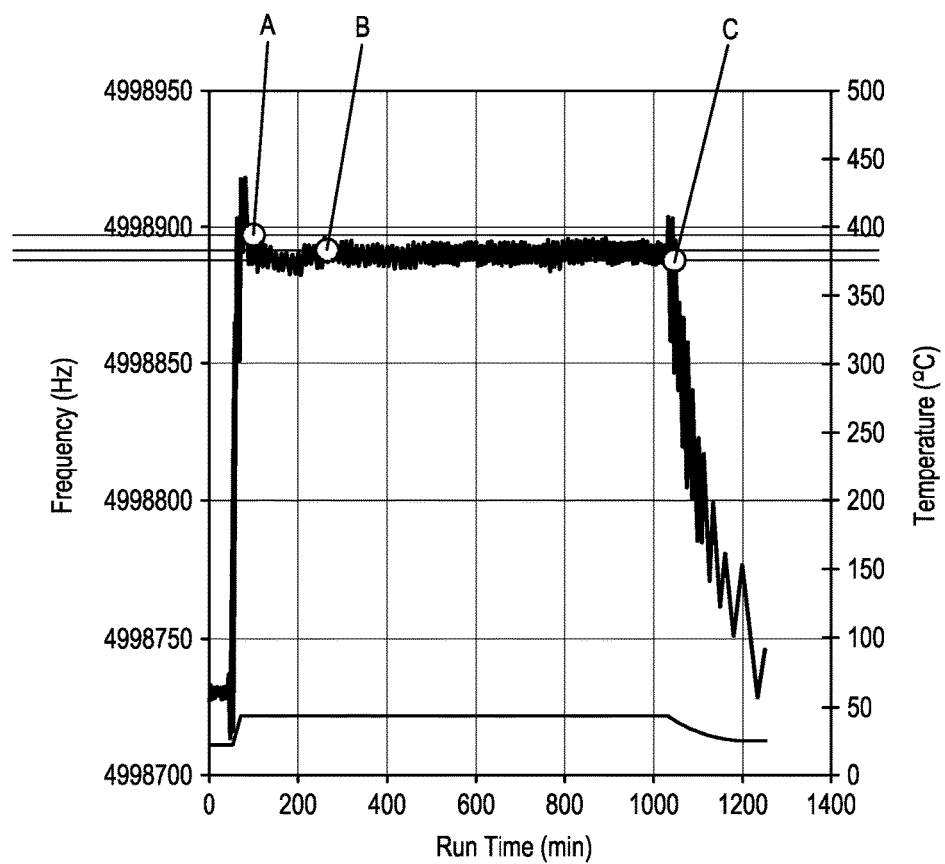
FIG. 2 shows an example of potential locations for sampling the frequency of a quartz crystal during aging of a sample.

Although the temperature profile in FIG. 1 could be effective in determining a frequency shift, determining the frequency shift accurately can pose some difficulties. Some difficulties relate to the problem that the ambient temperature for the baseline could vary over the course of the test. If for some reason the "ambient" temperature changes between the beginning and ending of the test, the measured frequency shift for the quartz crystal could be altered simply due to the use of inconsistent temperatures. If instead the elevated temperature is used for determining the frequency shift, determining when to start and end the frequency determination for both the initial frequency and the shifted frequency could be dependent on choices made by the operator of a test, leading to inconsistent results. FIG. 2 shows an example of the difficulty in selecting the appropriate location for starting the characterization of the frequency at the elevated temperature for a QCM apparatus characterization run performed at 43° C. In FIG. 2, three horizontal lines are shown, along with a highlighted point indicating the basis for selecting the lines. As shown in FIG. 2, depending on choices made by an operator, either point A or point B might be selected as an appropriate starting point for determining the frequency change for a quartz crystal disposed in the sample. Relative to the end point "C" shown in FIG. 2, selection of point A versus point B can alter the detected frequency change by more than 10 Hz, or alternatively by more than 25% of the frequency change that would indicate a sample that would fail a breakpoint stability test. Thus, it can be desirable to have an improved method for selecting the frequencies used for detecting the frequency change for a sample.

The potential inconsistencies due to operator choices can be reduced or minimized by using an alternative type of temperature profile for characterizing a sample. In the alternative temperature profile, a sample is initially heated to a temperature above ambient but below the temperature for inducing reactions and/or degradation. The sample can be maintained at this initial temperature for a period of time to establish a baseline frequency for the quartz crystal. By heating the sample prior to obtaining the baseline frequency, a controlled temperature can be established for the baseline frequency that is independent of the ambient environment. The temperature the sample is heated to for establishing the baseline frequency can be from about 25° C. to about 45° C., or about 25° C. to about 40° C., or about 27° C. to about 45° C., or about 27° C. to about 40° C., or about 25° C. to about 35° C., or about 27° C. to about 35° C., or about 30° C. to about 40° C., or about 30° C. to about 35° C.

The period of time for establishing the baseline frequency can be any convenient period of time, such as about 5 minutes to about 24 hours. In some aspects, the period of time for establishing the baseline frequency can be short relative to the total desired time for characterizing the sample, such as (for example) a time period of about 5 minutes to about 2 hours, or about 5 minutes to about 1.5 hours, or about 10 minutes to about 3 hours, or about 10 minutes to about 2 hours, or about 10 minutes to about 1.5 hours, or about 20 minutes to about 3 hours, or about 30 minutes to about 3 hours, or about 30 minutes to about 2 hours. During this initial period, a frequency measurement for the quartz crystal can be obtained at any convenient interval within the time period, such as obtaining a frequency measurement once per minute, or once every few minutes, or once every few seconds, or multiple times per second. The frequency measurements obtained during this initial period can be used in whole or in part for determining the baseline frequency. For example, once the sample reaches the initial temperature, all frequency measurements obtained at that temperature can be used to determine the baseline frequency, or a portion of the measurements can be used. Examples of using a portion of the measurements can include using all measurements after an initial stabilization period for the temperature to determine an average frequency, or using only every second or every third measurement that is obtained to determine an average frequency, or any other convenient scheme for determining a baseline frequency for the quartz crystal based on the measured values.

After determining the baseline frequency at the initial temperature, the sample can be heated to at least one higher temperature between about 40° C. and about 100° C. The sample can be held at each of the higher temperatures for any convenient period of time, so long as the overall profile can be repeated. In some aspects, the sample can be heated to a single higher temperature between 40° C. and 1.00° C. (or between about 45° C. and about 100° C.) for a period of time. In other aspects, the sample can be heated to and held at two or more temperatures (i.e., a plurality of temperatures) between about 40° C. and 100° C. for optionally independently selected periods of time. Any of the temperature ranges noted above can be used for selecting the single higher temperature or the plurality of higher temperatures. Thus, examples of temperature ranges for the higher temperature(s) include, but are not limited to, about 45° C. to about 90° C., or about 45° C. to about 80° C., or about 50° C. to about 100° C., or about 50° C. to about 90° C., or about 60° C. to about 100° C., or about 60° C. to about 90° C., or about 50° C. to about 80° C., or about 60° C. to about 80° C. A suitable total amount of time for holding the sample at the increased temperature(s) can be about 5 hours to about 24 hours, or about 5 to 18 hours, or about 8 to 20 hours, or about 8 to 18 hours, or about 5 to 16 hours, or about 8 to 16 hours, or about 10 to 20 hours, or about 10 to 18 hours, or about 10 to 16 hours, or about 12 to 20 hours, or about 12 to 18 hours, or about 12 to 16 hours.

After holding the sample at the one or more elevated temperatures for a suitable period of time the sample can be returned to the initial temperature that was used for measuring the baseline frequency. The frequency for comparison with the baseline frequency can then be obtained using a procedure similar to the procedure for obtaining the baseline frequency. The difference between the baseline frequency and the second or final frequency corresponds to a frequency shift for the quartz crystal disposed in the sample based on the heating profile.

Figure 3A:
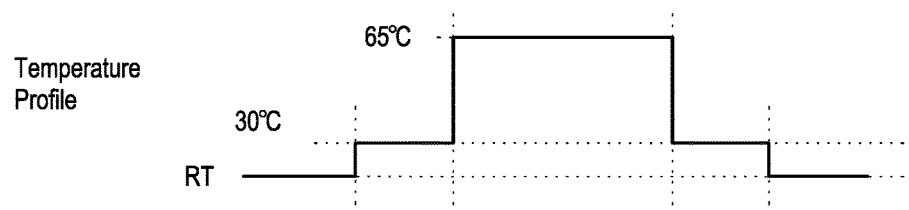
FIGS. 3A and 3B show an example of a temperature profile (FIG. 3A) for determining a breakpoint stability of a sample using a quartz crystal microbalance apparatus and potential times for sampling the frequency of the quartz crystal (FIG. 3B).
Figure 3B:
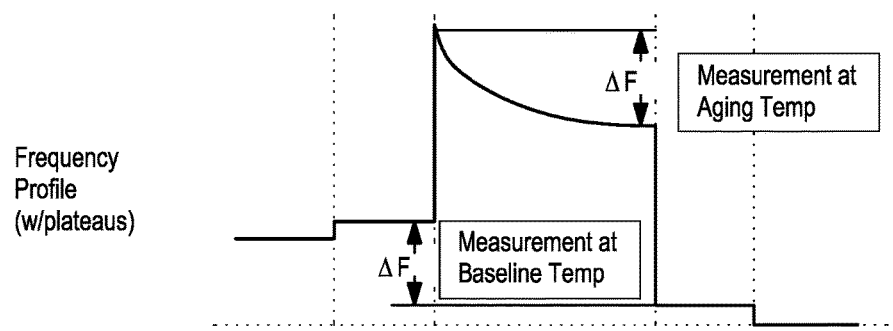
Figure 4:
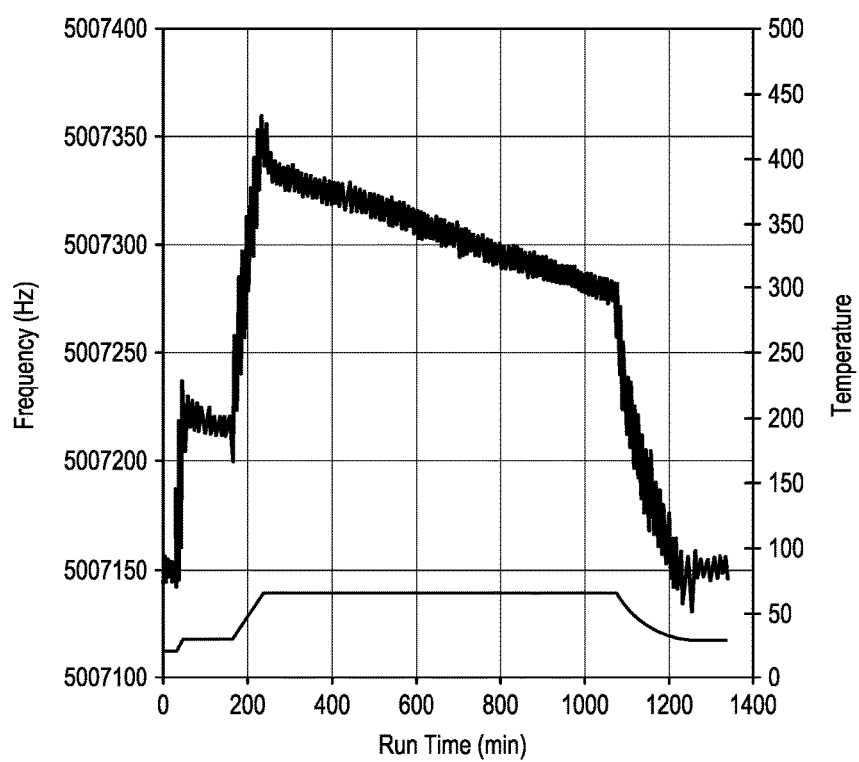
FIG. 4 shows frequency values for a quartz crystal microbalance apparatus operated according to the temperature profile shown in FIG. 3A.

FIG. 3A shows an example of a heating profile that includes a baseline profile and a higher temperature. FIG. 3B demonstrates the advantage in terms of establishing a reliable set of frequencies for determining a frequency shift. FIG. 4 shows the resulting frequency measurements for a quartz crystal for a sample heated according to a profile similar to FIG. 3A. For the example shown in FIGS. 3 and 4, a sample was initially heated to 30° C. and held at that temperature for about an hour to establish a baseline frequency. The sample was then heated to 65° C. and held at that temperature for about 14 hours. The sample was then cooled or returned to a temperature of 30° C. for about an hour to measure a final frequency for determining the frequency shift. The schematic example of the frequency measurements shown in FIG. 3B shows the advantage of determining the frequency shift using a temperature above ambient for establishing a baseline frequency. In the application of this method for characterizing the frequency change as shown in FIG. 4, the quartz crystal disposed in the sample shown in FIG. 4 exhibited a frequency shift of about 63 Hz, indicating that the sample would fail a breakpoint stability test.

Figure 5:
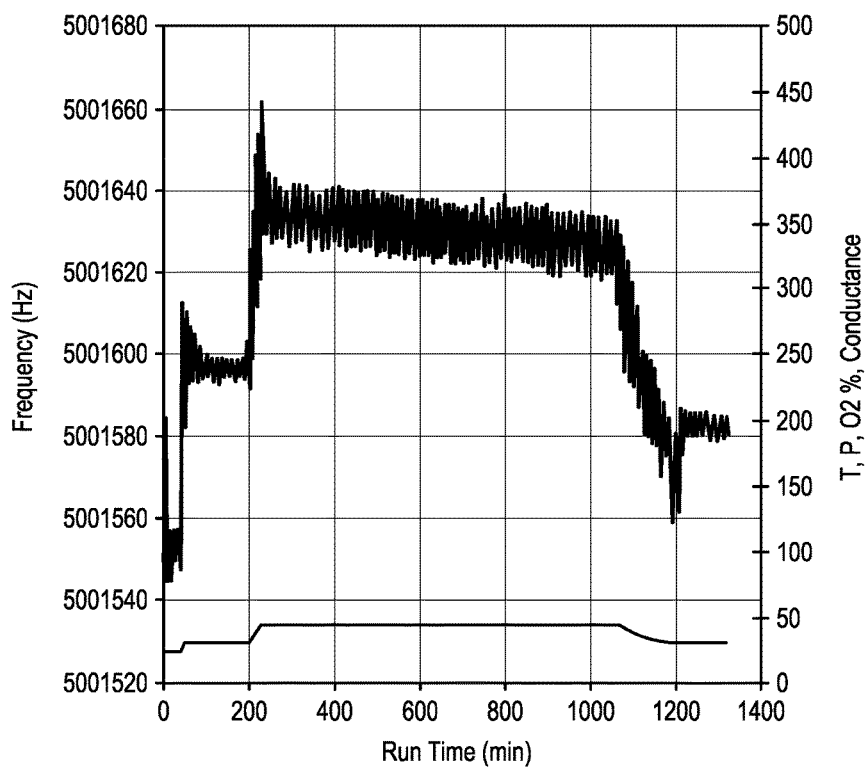
FIG. 5 shows frequency values for a sample characterized in a quartz crystal microbalance apparatus operated according to an alternative temperature profile.

The same type of sample tested in FIGS. 3 and 4 was also tested using a lower temperature profile, involving an initial temperature of 30° C. and a higher temperature of 43° C. Under this alternate temperature profile, the 14 hour heating time was insufficient to identify the sample as being a sample that would fail a breakpoint stability test. FIG. 5 shows the temperature profile and frequency measurements from the alternate profile. As shown in FIG. 5, the alternate temperature profile resulted in only an 18 Hz frequency shift.

Figure 6:
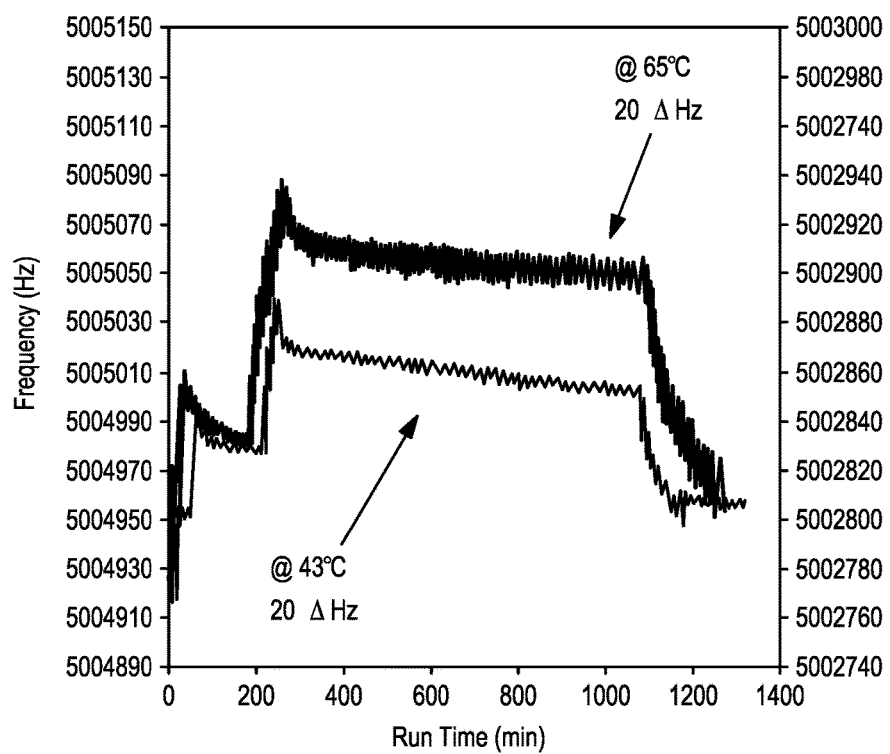
FIG. 6 shows frequency values for a sample characterized in a quartz crystal microbalance apparatus according to a temperature profile with an aging temperature of 43° C. (lower curve, right hand axis) and a temperature profile with an aging temperature of 65° C. (higher curve, left hand axis).

In contrast to FIGS. 4 and 5, for a sample that will satisfy breakpoint stability, the temperature profile including 43° C. and the temperature profile including 65° C. provide similar results. FIG. 6 shows measured frequency values for exposing a jet fuel sample that satisfies a breakpoint stability test to both heating profiles in a QCM apparatus. As shown in FIG. 6, the sample exhibits about a 20 Hz shift under both temperature profiles. This demonstrates that for a stable jet fuel sample, the amount of deposition on the quartz crystal is similar under both temperature profiles.

Kerosene or Jet Fractions from Pre-Refined Crude Sources

In some aspects, a jet fuel product (and/or fraction for incorporation into a product) characterized according to the methods described herein can be derived from a crude fraction that boils in the kerosene boiling range. In other aspects, a jet fuel can be at least partially derived from a crude fraction that boils in the kerosene boiling range. A fraction boiling in the kerosene boiling range can have an initial boiling point of at least about 28.4° F. (1.40° C.) and a final boiling point of about 572° F. (300° C.) or less. An initial boiling point refers to a temperature at the instant the first drop of condensate falls from the lower end of the condenser tube in a distillation apparatus, while a final boiling point refers to a final or maximum temperature after the evaporation of all liquid from the bottom of the distillation flask. In a conventional crude oil, the kerosene fraction of the crude typically contains only a few types of heteroatoms and/or functional groups. For example, a conventional kerosene fraction may contain sulfur, nitrogen, and olefins. Such conventional kerosene fractions are believed to be relatively stable over time if stored at standard temperature and pressure. Such stability for a kerosene fraction being considered for use as a jet fuel fraction can be confirmed using stability testing, such as by using the tests and standards identified in ASTM D3241 and/or D1655.

An increasing number of the petroleum sources being used today represent heavier and/or non-conventional sources. For some heavier crude oil sources, the oil may be difficult to remove from the ground. One way to facilitate removal of such oil is to add a diluent down well. When the diluent is pumped back into the petroleum source, flow characteristics of the oil are improved by producing a lower viscosity product. One option for generating a diluent is to remove a portion of the oil and process the portion in a coker or another type of cracking apparatus. Generating the diluent from oil removed from the well allows the diluent generation to be sustained from the oil present at a well head. A coker is typically used to generate the diluent. A petroleum crude fraction extracted by this method is sometimes referred to as a pre-refined crude, as refining processes (e.g., distillation, coking, hydrotreating, blending) have been applied to this crude before it is reblended into a pumpable oil and shipped to a refiner. These crudes are also referred to as synthetic crudes.

A pre-refined crude oil is defined herein as a crude where at least a portion of the crude oil has been cracked or otherwise converted using one or more refining processes prior to shipment of the crude to a refinery. A fraction derived from a pre-refined crude oil is defined herein as a fraction where at least 5 vol % of the fraction corresponds to molecules formed during the cracking or other conversion processes prior to shipment to a refinery. For example, at least 10 vol % of the fraction can be molecules formed during cracking or conversion prior to shipment to a refinery, or at least 25 vol % of the fraction, or at least 50 vol % of the fraction. One way to a define a molecule formed during a conversion process prior to shipment to a refinery is based on conversion of molecules relative to a boiling point. For example, molecules formed during a conversion process can be defined as molecules formed as a result of conversion of feed from a temperature above 300° C. to below 300° C., or conversion from above 350° C. to below 350° C., or conversion from above 370° C. to below 370° C., or conversion relative to any other convenient conversion temperature.

Any convenient amount of material derived from a pre-refined crude oil from a crude source can be incorporated into the sample for testing. Thus, the amount of pre-refined crude oil (i.e., material derived from a pre-refined crude oil) in a sample can be at least 5 vol. % of the sample, or at least 10 vol %, or at least 25 vol %, or at least 50 vol %, or at least 75 vol %. Additionally or alternatively, the amount of pre-refined crude can be 100 vol % or less, or about 95 vol. % or less of the sample, or about 90 vol. % or less, or about 75 vol % or less, or about 50 vol % or less, or about 25 vol % or less. The amount of pre-refined crude oil is determined at least in part by the desired amount of pre-refined crude in a corresponding desired jet fuel product. If the properties of a kerosene fraction, jet fuel fraction, or jet fuel finished product derived from pre-refined crude are suitable, a sample for testing could be entirely composed of material derived from a pre-refined crude.

As an alternative, the amount of pre-refined crude can be defined based on the vol % of pre-refined crude oil in a crude oil feedstock prior to distillation or fractionation to form a jet fuel or kerosene fraction. For example, a pre-refined crude oil feedstock and a conventional crude oil feedstock can be combined prior to fractionation of the feedstocks to form a jet fuel or kerosene boiling range fraction. The combined crude oil feedstock is then fractionated to produce the desired jet fuel or kerosene boiling range fraction. Depending on the embodiment, the amount of pre-refined crude oil in a feedstock prior to forming a jet fuel fraction or kerosene fraction can be at least 5 vol % of the feedstock, or at least 10 vol %, or at least 25 vol %, or at least 50 vol %, or at least 75 vol %. Additionally or alternatively, the amount of pre-refined crude can be about 95 vol % or less of the feedstock, or about 90 vol. % or less, or about 75 vol % or less, or about 50 vol % or less, or about 25 vol % or less. In situations where weight percentage is more convenient, a suitable feedstock and/or sample can include a weight percentage corresponding to any of the above percentages, such as at least about 5 wt %, or at least about 25 wt %, or about 95 wt % or less, or about 75 wt % or less. It is noted that if the pre-refined crude oil is combined with a conventional feed prior to fractionation, the percentage of material derived from a pre-refined crude oil in the jet fuel fraction may differ from the pre-refined crude oil percentage in the feedstock delivered to fractionation. In some aspects, the volume percentage of material derived from a pre-refined crude in a crude feed prior to distillation will be comparable to or more preferably greater than the amount of pre-refined crude material in a corresponding kerosene or jet fuel product that is derived from such a crude feed.

If a sample for testing comprises a portion derived from a pre-refined crude and a conventional portion, any convenient type of conventional portion can be used. The conventional portion may be from a mineral source, an approved biologically-derived source, or a combination thereof. Typical conventional portions have a boiling range corresponding to an initial boiling point of at least about 284° F. (140° C.) and a final boiling point of less than or equal to about 572"F (300° C.). The sulfur content of a conventional jet fuel portion is 3000 wppm or less, such as about 1500 wppm or less or about 500 wppm or less. Preferably, the conventional portion satisfies the jet fuel specifications in D1655 prior to combining the conventional portion with the portion derived from a pre-refined crude.

In some aspects, a pre-refined crude oil can be a pre-refined crude oil that has been cracked or otherwise converted in a reaction environment containing less than 50 psig (345 kPag) of hydrogen, such as an environment containing less than 14 psig (97 kPag) of hydrogen. Such a pre-refined crude oil represents a crude oil that has not been subjected to hydroprocessing prior to shipment to a refinery. Avoiding processes that include added hydrogen is beneficial due to the costs of providing hydrogen at a well head or crude oil production site. A fraction derived from a non-hydroprocessed pre-refined crude is defined herein as a fraction where at least 5 vol % of the fraction corresponds to molecules formed during the cracking or other conversion process in a hydrogen-limited environment as described above for making a non-hydroprocessed pre-refined crude. For example, at least 10 vol % of the fraction can be molecules formed during cracking or conversion in a hydrogen-limited environment, or at least 25 vol. % of the fraction, or at least 50 vol % of the fraction.

A portion of the crude oil processed in a coker (or other conversion process) to form a pre-refined crude oil will result in a pre-refined crude product fraction that boils in the kerosene boiling range, such as a fraction with an initial boiling point of at least about 284° F. (140° C.) and a final boiling point of about 572° F. (300° C.) or less. As a result, the boiling range of this material is suitable for incorporation into a jet fuel fraction. However, the composition of the kerosene boiling range material in a fraction derived from a pre-refined crude oil differs from the composition of a virgin kerosene fraction. In contrast to a kerosene fraction derived from a conventional crude oil, a kerosene boiling range fraction derived from a pre-refined crude oil can include and/or is primarily composed of species generated by cracking of a heavier boiling range fraction. As a result, a kerosene fraction derived from a pre-refined crude oil may contain heteroatoms and/or functional groups not present in a conventional kerosene fraction. For example, due to the cracking or other conversion in a hydrogen-limited environment used to form some types of pre-refined crude oils, the kerosene fraction from a pre-refined crude can contain elevated levels of functional groups with lower stability, such as terminal olefins or alkynes. The heteroatoms present in the kerosene fraction of a pre-refined crude may also be different in character. In a conventional crude oil, for example, a large percentage of the sulfur content of a kerosene fraction may be in the form of mercaptans or other molecules where the sulfur is incorporated into a molecule by a carbon-sulfur single bond. By contrast, the portion the kerosene fraction of a pre-refined crude oil can contain a greater variety of sulfur atom types, such as sulfur atoms incorporated into di-benzothiophenes or other aromatic sulfur compounds. For example, incomplete cracking of the original crude may result in compounds where sulfur is incorporated with linkages other than carbon-sulfur single bonds. Similarly, the types of nitrogen compounds present in pre-refined crude kerosene fraction may correspond to a greater variety of compounds than would be expected in a conventional (mineral) kerosene boiling range fraction.

One side effect from the increased variety of species in a kerosene fraction derived from a pre-refined crude is that the kerosene fraction can have unsatisfactory breakpoint stability over time. This may be due to individual contaminants being more reactive, or the increased variety of functional groups and heteroatoms present in kerosene derived from a pre-refined crude may interact with each other to produce a more highly reactive environment. Regardless of the cause, the decreased breakpoint stability of a kerosene fraction derived from a pre-refined crude oil means that the properties of such a kerosene fraction are likely to have a greater variability over time as compared to a conventional kerosene fraction. In some aspects, a kerosene fraction having an unsatisfactory breakpoint stability over time can correspond to a kerosene fraction where the breakpoint changes by more than 10° C. after 1 year of storage and/or under conditions that simulate a year of storage at standard temperature of about 20° C. Alternatively, a kerosene fraction having an unsatisfactory breakpoint stability can correspond to a kerosene fraction where the breakpoint changes by more than 6° C. after 6 months of storage and/or under conditions that simulate 6 months of storage.

The lower breakpoint stability of kerosene fractions derived from pre-refined to crude oils poses difficulties for the use of such kerosene fractions in jet fuel applications. Jet fuel products are typically qualified, with regard to thermal stability, using an ASTM standard test (ASTM D3241) to determine if the product properties satisfy the thermal stability specifications in ASTM D1655. The ASTM D3241 test is a "pass/fail" type test, meaning that a proposed jet fuel fraction is either qualified or not qualified for use. For jet fuel fractions formed from conventional crudes, such a "pass/fail" stability test works well as low boiling distillate fractions from conventional crudes (such as fractions suitable for use as a jet fuel product) have good breakpoint stability over time. For the fractions with uncertain breakpoint stability that are typically generated from pre-refined crudes, however, the single pass/fail breakpoint stability test does not provide information about whether a proposed jet fuel fraction will remain viable after a period of storage.

FIG. 1 shows an example of applying the QCM method to a jet fuel sample containing at least a portion derived from a pre-refined crude. In the example shown in FIG. 1, 47 wt % of the sample corresponded to two different pre-refined crude sources. The method of performing the QCM measurement is similar for samples containing pre-refined crude portions, as the same 40 Hz frequency shift can be used as the threshold for identifying a sample that has sufficient breakpoint stability versus a sample that does not.

Kerosene or Jet Fractions from Cracking Processes

In some aspects, a jet fuel product and/or fraction for incorporation into a product characterized according to the methods described herein can be derived from a crude fraction that boils in the kerosene boiling range. In other aspects, a jet fuel can be at least partially derived from a crude fraction that boils in the kerosene boiling range. A fraction boiling in the kerosene boiling range can have an initial boiling point of at least about 284° F. (140° C.) and a final boiling point of about 572° F. (300° C.) or less. An initial boiling point refers to a temperature at the instant the first drop of condensate falls from the tower end of the condenser tube in a distillation apparatus, while a final boiling point in refers to a final or maximum temperature after the evaporation of all liquid from the bottom of the distillation flask. In a conventional crude oil, the kerosene fraction of the crude typically contains only a few types of heteroatoms and/or functional groups. For example, a conventional kerosene fraction may contain sulfur, nitrogen, and olefins. Such conventional kerosene fractions are believed to be relatively stable over time if stored at standard temperature and pressure. Such stability for a kerosene fraction being considered for use as a jet fuel fraction can be confirmed using stability testing, such as by using the tests and standards identified in ASTM D3241 and/or D1655.

Although a portion of a crude oil or crude fraction may boil in the kerosene (or jet fuel) boiling range, a fraction having a boiling point range within the kerosene boiling range can also be created by various types of cracking and/or conversion processes. For example, in a refinery setting, a variety of processes can be used to crack or otherwise convert compounds within a petroleum feed from higher boiling compounds to lower boiling compounds. A fraction at least partially derived from such a cracking process can be referred to as a cracked fraction. Some processes correspond to processes where cracking occurs with a reduced or minimized amount of hydrogen present. Other processes can correspond to hydrogen-assisted cracking processes, such as hydrocracking type processes. In this description, a cracking process that is performed in an atmosphere containing about 50 psig (345 kPa) or less of hydrogen is defined as a hydrogen-limited cracking process. Processes where the cracking is performed in the presence of greater than 50 psig (345 kPa) of hydrogen are defined as hydrogen-assisted cracking processes. In this discussion, a potential kerosene or jet fuel fraction is considered to have been derived from a hydrogen-limited cracked feedstock if prior to fractionation to form a fraction having a boiling range of 140° C. to 300° C., the feedstock is exposed to a process having a hydrogen partial pressure of about 50 psig (345 kPa) or less that converts at least 5 wt % of the feed relative to a defined conversion temperature, or at least about 10 wt %, or at least about 15 wt %. In this discussion, a potential kerosene or jet fuel fraction is considered to have been derived from a hydrogen-assisted cracked feedstock if, prior to fractionation to form a fraction having a boiling range of 140° C. to 300° C., the feedstock is exposed to a process having a hydrogen partial pressure of greater than 50 psig (345 kPa) that converts at least 15 wt % of the feed relative to a defined conversion temperature, or at least about 20 wt %, or at least about 25 wt %. The defined conversion temperature can be any convenient conversion, such as a conversion temperature between about 150° C. and about 400° C. It is noted that the conversion temperature can be a conversion temperature within the 140° C. to 300° C. boiling range, or a conversion temperature outside of that boiling range, such as a 700° F. (371° C.) conversion temperature that is often used for characterization of the severity of a hydrocracking process for forming lubricant base oils. A cracked fraction or other cracked feedstock formed according to a hydrogen-assisted cracking process or a hydrogen-limited cracking process as described herein is defined herein as a fraction where at least 5 vol % of the fraction corresponds to molecules formed during the cracking or other conversion process. For example, at least 10 vol % of the cracked fraction can be molecules formed during cracking or conversion, or at least 25 vol % of the cracked fraction, or at least 50 vol % of the cracked fraction.

Cracking processes with about 50 psig (345 kPa) or less of hydrogen in the environment for the cracking reaction cracking (i.e., hydrogen-limited cracking processes) can correspond to processes for converting low value, high boiling crude fractions and/or other low value, high boiling feeds into lower boiling range compounds that may be suitable for use as fuels. For example, processes such as coking, visbreaking, and other thermal cracking processes can provide a method for converting a high boiling range feed with a tow ratio of hydrogen to carbon into at least a) lower boiling feed portions with an increased hydrogen to carbon ratio, and b) coke. As another type of example, fluid catalytic cracking processes can be used to enhance thermal cracking by use of a catalyst but without the presence of substantial amounts of hydrogen.

The various types of catalytic and/or thermal cracking processes that operate without a substantial amount of added hydrogen generally produce naphtha and distillate fuel boiling range fractions as a substantial portion of the process effluent. For example, the naphtha portions from such hydrogen-limited processes can be referred to as catalytic naphthas or cat naphthas. The naphtha portions from such cracking processes can be considered as being composed of a "light cat naphtha" portion and a "heavy cat naphtha" portion. A heavy cat naphtha can have an initial boiling point that is at least about the 284° F. (140° C.) minimum boiling point for a kerosene fraction. Similarly, the end boiling point for a heavy cat naphtha can be less than the 572° F. (300° C.) end boiling point for a jet fuel fraction. More generally, the typical fractionation scheme used for separating products from a cracking process can be modified to generate a fraction with both an initial boiling point and a final boiling point that is within the 140° C.-300° C. boiling range.

Hydrogen-assisted cracking processes, such as hydrocracking, can also be used for conversion of a feed to lower boiling compounds. Feeds treated using a hydrogen-assisted cracking process can often have a higher initial hydrogen-to-carbon ratio than a typical feed for a hydrogen-limited cracking process. However, this is often based more on economic considerations than technical considerations. Hydrogen-assisted cracking processes can also be used to generate either heavy cat naphtha boiling range fractions within the 140° C.-300° C. boiling range and/or kerosene fractions within that boiling range.

Any convenient amount of material derived from a cracked feedstock can be incorporated as a cracked fraction into a sample for testing. Thus, the amount of cracked fraction (i.e., material derived from a feed exposed to hydrogen-assisted and/or hydrogen-limited cracking conditions) in a sample can be at least 5 vol % of the sample, or at least 10 vol %, or at least 25 vol %, or at least 50 vol %, or at least 75 vol %. Additionally or alternatively, the amount of cracked fraction can be 100 vol % or less, or about 95 vol % or less of the sample, or about 90 vol % or less, or about 75 vol % or less, or about 50 vol % or less, or about 25 vol % or less. The amount of cracked fraction is determined at least in part by the desired amount of cracked fraction in a corresponding desired jet fuel product. If the properties of a kerosene fraction, jet fuel fraction, or jet fuel finished product derived from a cracked fraction are suitable, a sample for testing could be entirely composed of material derived from a cracked fraction.

As an alternative, the amount of cracked material in a fraction can be defined based on the vol % of cracked feed in a feedstock prior to distillation or fractionation to form a jet fuel or kerosene fraction. For example, a cracked feed and a non-cracked feed can be combined prior to fractionation of the feeds to form a jet fuel or kerosene boiling range fraction. The combined feedstock is then fractionated to produce the desired jet fuel or kerosene boiling range fraction. Depending on the embodiment, the amount of cracked feed in a feedstock prior to forming a jet fuel fraction or kerosene fraction can be at least 5 vol % of the feedstock, or at least 10 vol %, or at least 25 vol %, or at least 50 or at least 75 vol %. Additionally or alternatively, the amount of cracked feed can be about 95 vol % or less of the feedstock, or about 90 vol % or less, or about 75 vol % or less, or about 50 vol % or less, or about 25 vol % or less. In situations where weight percentage is more convenient, a suitable feedstock and/or sample can include a weight percentage corresponding to any of the above percentages, such as at least about 5 wt %, or at least about 25 wt %, or about 95 wt % or less, or about 75 wt % or less. It is noted that if the cracked feed is combined with a non-cracked feed prior to fractionation, the percentage of material derived from a cracked feed in the jet fuel fraction may differ from the cracked feed percentage in the feedstock delivered to fractionation. In some aspects, the volume percentage of material derived from a cracked feed in a feedstock prior to distillation will be comparable to or more preferably greater than the amount of cracked fraction in a corresponding kerosene or jet fuel product that is derived from such a crude feed.

If a sample for testing comprises a portion derived from a cracked feed and a conventional portion, any convenient type of conventional portion can be used. The conventional portion may be from a mineral source, an approved biologically-derived source, or a combination thereof. Typical conventional portions have a boiling range corresponding to an initial boiling point of at least about 284° F. (140° C.) and a final boiling point of less than or equal to about 572° F. (300° C.). The sulfur content of a conventional jet fuel portion is 3000 wppm or less, such as about 1500 wppm or less or about 500 wppm or less. Preferably, the conventional portion satisfies the jet fuel specifications in D1655 prior to combining the conventional portion with the portion derived from a pre-refined crude.

For a feedstock containing cracked feed, a fraction can be formed that has a boiling range suitable for incorporation into a jet fuel fraction i.e., 140° C. to 300° C.). However, the composition of the kerosene boiling range material in a fraction derived from a cracked feed can differ from the composition of a virgin kerosene fraction. In contrast to a kerosene fraction derived from a conventional crude oil, a kerosene boiling range fraction derived from a cracked feed can include and/or is primarily composed of species generated by cracking of a heavier boiling range fraction. As a result, a kerosene fraction derived from a cracked feed may contain heteroatoms and/or functional groups not present in a conventional kerosene fraction. For example, due to the cracking or other conversion in a hydrogen-limited environment used to form some types of cracked feeds, the kerosene fraction from a cracked feed can contain elevated levels of functional groups with lower stability, such as terminal olefins or alkynes. The heteroatoms present in the kerosene fraction of a cracked feed may also be different in character. In a conventional crude oil, for example, a large percentage of the sulfur content of a kerosene fraction may be in the form of mercaptans or other molecules where the sulfur is incorporated into a molecule by a carbon-sulfur single bond. By contrast, the portion the kerosene fraction of a cracked feed can contain a greater variety of sulfur atom types, such as sulfur atoms incorporated into di-benzothiophenes or other aromatic sulfur compounds. For example, incomplete cracking of the original crude may result in compounds where sulfur is incorporated with linkages other than carbon-sulfur single bonds. Similarly, the types of nitrogen compounds present in a cracked feed may correspond to a greater variety of compounds than would be expected in a conventional (mineral) kerosene boiling range fraction.

One side effect from the increased variety of species in a kerosene fraction derived from a cracked fraction or cracked feed is that the kerosene fraction can have unsatisfactory breakpoint stability over time. This may be due to individual contaminants being more reactive, or the increased variety of functional groups and heteroatoms present in kerosene derived from a pre-refined crude may interact with each other to produce a more highly reactive environment. Regardless of the cause, the decreased breakpoint stability of a kerosene fraction derived from a cracked feed means that the properties of such a kerosene fraction are likely to have a greater variability over time as compared to a conventional kerosene fraction. In some aspects, a kerosene fraction having an unsatisfactory breakpoint stability over time can correspond to a kerosene fraction where the breakpoint changes by more than 10° C. after 1 year of storage and/or under conditions that simulate a year of storage at standard temperature of about 20° C. Alternatively, a kerosene fraction having an unsatisfactory breakpoint stability can correspond to a kerosene fraction where the breakpoint changes by more than 6° C. after 6 months of storage and/or under conditions that simulate 6 months of storage.

The lower breakpoint stability of kerosene fractions derived from cracked feeds poses difficulties for the use of such kerosene fractions in jet fuel applications. Jet fuel products are typically qualified, with regard to thermal stability, using an ASTM standard test (ASTM D3241) to determine if the product properties satisfy the thermal stability specifications in ASTM D1655. The ASTM D3241 test is a "pass/fail" type test, meaning that a proposed jet fuel fraction is either qualified or not qualified for use. For jet fuel fractions formed from conventional crudes, such a "pass/fail" stability test works well as low boiling distillate fractions from conventional crudes (such as fractions suitable for use as a jet fuel product) have good breakpoint stability over time. For the fractions with uncertain breakpoint stability that are typically generated from cracked feeds, however, the single pass/fail breakpoint stability test does not provide information about whether a proposed jet fuel fraction will remain viable after a period of storage.

Hydrotreatment or Other Upgrading

Another potential benefit of the more rapid breakpoint stability characterization provided by using a QCM apparatus is the ability to make adjustments in processing of potential jet fuel fractions that initially do not have sufficient stability. For example, if a pre-refined crude sample (and/or a cracked feed sample) does not have sufficient breakpoint stability, the pre-refined crude (and/or cracked feed) can be blended with another sample that does have sufficient stability, or the sample can be hydroprocessed (such as by hydrotreatment) and/or chemically treated, or a combination thereof. Hydroprocessing and/or chemical treatment of a sample can increase the total amount of the available kerosene pool that can be used directly for jet fuel, while blending can be used to increase the amount of available kerosene for jet fuel by blending lower stability fractions with other kerosene fractions that have better stability.

Blending of crude samples can provide a potential method for incorporating a (pre-refined) sample with questionable stability into a more stable kerosene sample to form an overall sample that satisfies breakpoint and breakpoint stability tests. For a sample that cannot satisfy a breakpoint stability test individually, the amount of the sample that can be used in a blend to form a sufficiently stable sample is highly variable. The amount of a sample that fails the breakpoint stability test that can be used in a blend that will satisfy breakpoint stability testing can be from 1 vol % to 75 vol %. For example, the amount of the sample that fails the breakpoint stability test in a blend can be about 1 vol % to about 50 vol %, or about 1 vol % to about 35 vol %, or about 1 vol % to about 25 vol %, or about 1 vol % to about 15 vol %, or about 5 vol % to about 50 vol %, or about 5 vol. % to about 35 vol %, or about 5 vol % to about 25 vol %, or about 5 vol % to about 15 vol %.

Another option for upgrading a jet fuel fraction is, for example, to hydroprocess the jet fuel fraction, expose the jet fuel fraction to chemical treating, or a combination thereof. Chemical treating can refer to, for example, treating a fraction with acid in order to remove nitrogen compounds from the fraction.

In this discussion, hydroprocessing is a type of hydrogen treating. A wide range of hydroprocessing conditions are potentially suitable for use, as even mild hydroprocessing conditions may produce a benefit in the properties of the jet fuel fraction. During hydroprocessing, a feedstock that is partially or entirely composed of a jet fuel boiling range fraction is treated in a hydrotreatment (or other hydroprocessing) reactor that includes one or more hydrotreatment stages or beds. Optionally, the reaction conditions in the hydrotreatment stage(s) can be conditions suitable for reducing the sulfur content and/or other heteroatom content of the feedstream, such as conditions suitable for reducing the sulfur content of the feedstream to about 3000 wppm or less, or about 1000 wppm or less, or about 500 wppm or less. The reaction conditions can include an LHSV of 0.1 to 20.0 hr$^{-1}$, a hydrogen partial pressure from about 50 psig (0.34 MPag) to about 3000 psig (20.7 MPag), a treat gas containing at least about 50% hydrogen, and a temperature of from about 450° F. (232° C.) to about 800° F. (427° C.). Preferably, the reaction conditions include an LHSV of from about 0.3 to about 5 hr$^{-1}$, a hydrogen partial pressure from about 100 psig (0.69 MPag) to about 1000 psig (6.9 MPag), and a temperature of from about 700° F. (371° C.) to about 750° F. (399° C.).

Optionally, a hydrotreatment reactor can be used that operates at relatively low total pressure values, such as total pressures less than about 800 psig (5.5 MPag). For example, the pressure in a stage in the hydrotreatment reactor can be at least about 200 psig (1.4 MPag), or at least about 300 psig (2.1 MPag), or at least about 400 psig (2.8 MPag), or at least about 450 psig (3.1 MPag). The pressure in a stage in the hydrotreatment reactor can be about 700 psig (4.8 MPag) or less, or about 650 psig (4.5 MPag) or less, or about 600 psig (4.1 MPa) or less.

The catalyst in a hydrotreatment stage can be a conventional hydrotreating catalyst, such as a catalyst composed of a Group VIB metal and/or a Group VIII metal on a support. Suitable metals include cobalt, nickel, molybdenum, tungsten, or combinations thereof. Preferred combinations of metals include nickel and molybdenum or nickel, cobalt, and molybdenum. Suitable supports include silica, alumina, and titanic.

In an aspect, the amount of treat gas delivered to the hydrotreatment stage can be based on the consumption of hydrogen in the stage. The treat gas rate for a hydrotreatment stage can be from about two to about five times the amount of hydrogen consumed per barrel of fresh feed in the stage. A typical hydrotreatment stage can consume from about 50 SCF/B (8.4 m$^3$/m$^3$) to about 1000 SCF/B (168.5 m$^3$/m$^3$) of hydrogen, depending on various factors including the nature of the feed being hydrotreated. Thus, the treat gas rate can be from about 100 SCF/B (16.9 m$^3$/m$^3$) to about 5000 SCPB (842 m$^3$/m$^3$). Preferably, the treat gas rate can be from about four to about five time the amount of hydrogen consumed. Note that the above treat gas rates refer to the rate of hydrogen flow. If hydrogen is delivered as part of a gas stream having less than 100% hydrogen, the treat gas rate for the overall gas stream can be proportionally higher.

In still other aspects, both blending and hydroprocessing and/or chemical treating can be used in any convenient combination to arrive at a hydroprocessed and/or treated blend that can satisfy a breakpoint stability test.

ADDITIONAL EMBODIMENTS

Embodiment 1

A method of characterizing a kerosene boiling range sample, comprising: disposing a quartz crystal in a vessel containing a kerosene boiling range sample; heating the kerosene boiling range sample to a baseline temperature; measuring a frequency of the quartz crystal at the baseline temperature during a first sampling period to obtain a baseline frequency; heating the kerosene boiling range sample to an aging temperature and maintaining the sample at the aging temperature for an aging period; returning the kerosene boiling range sample to the baseline temperature; and measuring the frequency of the quartz crystal at the baseline temperature during a second sampling period to obtain an aged frequency, a difference between the baseline frequency and the aged frequency being indicative of a stability of the kerosene boiling range sample.

Embodiment 2

The method of Embodiment it wherein the kerosene boiling range sample has a boiling range of about 140° C. to about 300° C.

Embodiment 3

The method of any of Embodiments 1 or 2, wherein the baseline temperature is about 25° C. to about 45° C., or about 27° C. to about 40° C., or at least about 30° C., or about 35° C. or less.

Embodiment 4

The method of any of the above embodiments, wherein the aging temperature is about 40° C. to about 100° C., or about 45° C. to about 90° C., or at least about 50° C., or at least about 60° C., or about 90° C. or less, or about 80° C. or less, or about 70° C. or less.

Embodiment 5

The method of any of the above embodiments, wherein the aging period is about 5 hours to about 24 hours, or about 8 hours to about 20 hours.

Embodiment 6

The method of any of the above embodiments, wherein the first sampling period is about 5 minutes to about 2.4 hours.

Embodiment 7

The method of any of the above embodiments, wherein measuring the baseline frequency comprises: sampling a frequency of the quartz crystal a plurality of times during at least a portion of the first sampling period; and determining the baseline frequency based on an average of at least a portion of the sampled frequency values from the at least a portion of the first sampling period.

Embodiment 8

The method of Embodiment 7, wherein measuring the aged frequency comprises: sampling a frequency of the quartz crystal a plurality of times during at least a portion of the second sampling period; and determining the aged frequency based on an average of at least a portion of the sampled frequency values from in the at least a portion of the first sampling period.

Embodiment 9

The method of Embodiment 8, wherein a time corresponding to the at least a portion of the first sampling period is the same as a time corresponding to the at least a portion of the second sampling period.

Embodiment 10

The method of any of the above embodiments, wherein the kerosene boiling range sample comprises a portion derived from a pre-refined crude oil, a portion derived from a cracked fraction, or a combination thereof.

Embodiment 11

The method of Embodiment 10, wherein the portion derived from the pre-refined crude oil, the portion derived from the cracked fraction, or the combination thereof comprises at least about 5 vol % of molecules formed during cracking or conversion in a hydrogen-limited environment, or at least about 10 vol %, or at least about 25 vol %, or at least about 50 vol %.

Embodiment 12

The method of Embodiments 10 or 11, wherein the cracked fraction is derived from a cracked feedstock where at least about 5 wt % of the cracked feedstock is converted relative to a conversion temperature based on exposure to hydrogen-limited cracking conditions, or at least about 10 wt %, or at least about 15 wt %, or at least about 25 wt %, or at least about 50 wt %.

Embodiment 13

The method of Embodiments 10 or 11, wherein the cracked fraction is derived from a cracked feedstock where at least about 15 wt % of the cracked feedstock is converted relative to a conversion temperature based on exposure to hydrogen-assisted cracking conditions, or at least about 20 wt %, or at least about 25 wt %, or at least about 50 wt %.

Embodiment 14

The method of any of the above embodiments, further comprising determining a breakpoint for a second kerosene boiling range sample, the kerosene boiling range sample and the second kerosene boiling range sample being derived from the same source, the breakpoint for the second kerosene boiling range sample being at least about 265° C., or at least about 275° C.

Embodiment 15

The method of Embodiment 14, wherein the kerosene boiling range sample and the second kerosene boiling range sample are formed by obtaining a portion of a distillate fraction; and splitting the portion of the distillate fraction to form at least the kerosene boiling range sample and the second kerosene boiling range sample.

Embodiment 16

The method of any of the above embodiments, wherein the difference between the baseline frequency and the aged frequency is about 39 Hz or less.

Embodiment 17

A method of characterizing a distillate boiling range sample, comprising: determining a breakpoint for a first sample of a distillate fraction, the distillate fraction having an initial boiling point of at least about 284° F. (140° C.) and a final boiling point of about 572° F. (300° C.) or less, at least a portion of the distillate fraction being derived from a pre-refined crude oil, a cracked fraction, or a combination thereof, the determined breakpoint being greater than about 265° C.; heating a second sample of the distillate fraction in a vessel of a quartz crystal microbalance apparatus to an aging temperature for an aging period, the quartz crystal microbalance apparatus comprising a quartz crystal, the quartz crystal being disposed in the second sample during the heating; measuring a baseline frequency and an aged frequency of the quartz crystal, the aged frequency being measured after maintaining the second sample of the distillate fraction at the aging temperature for an aging period, the baseline frequency being measured prior to maintaining the second sample of the distillate fraction at the aging temperature for the aging period, a difference between the baseline frequency and the aged frequency for the second sample being greater than or equal to a threshold frequency difference value; hydrotreating or chemical treating a third sample of the distillate fraction under effective treating conditions to form a treated third sample of the distillate fraction, the effective treating conditions optionally but preferably being effective hydrotreating conditions; heating at least a portion of the treated third sample of the distillate fraction in a vessel of a quartz crystal microbalance apparatus to the aging temperature for the aging period, the quartz crystal microbalance comprising a quartz crystal, the quartz crystal being disposed in the at least a portion of the treated third sample during the heating; and measuring a baseline frequency and an aged frequency for the at least a portion of the treated third sample of the distillate fraction using a quartz crystal microbalance apparatus, the aged frequency being measured after maintaining the treated third sample of the distillate fraction at the aging temperature tier the aging period, a difference between the baseline frequency and the aged frequency for the at least a portion of the treated third sample being less than the threshold frequency difference value.

Embodiment 18

The method of Embodiment 17, wherein a breakpoint of the treated third sample is at least about 265° C., or at least about 275° C.

Embodiment 19

The method of any of Embodiments 17 or 18, further comprising: obtaining a portion of the distillate fraction; and splitting the portion of the distillate fraction to form at least the first sample, the second sample, and the third sample.

Embodiment 20

The method of any of Embodiments 17 to 19, wherein the second sample and the at least a portion of the third treated sample are heated in the same vessel.

Embodiment 21

The method of any of Embodiments 17 to 20, wherein the at least a portion of the distillate fraction derived from the pre-refined crude oil, the cracked fraction, or the combination thereof comprises at least about 5 vol % of molecules formed during cracking or conversion in a hydrogen-limited environment, or at least about 10 vol %, or at least about 25 vol %, or at least about 50 vol %.

Embodiment 22

The method of any of Embodiments 17 to 21, wherein the cracked fraction is derived from a cracked feedstock where at least 5 wt % of the cracked feedstock is converted relative to a conversion temperature based on exposure to hydrogen-limited cracking conditions, or at least about 10 wt %, or at least about 15 wt %, or at least about 25 wt %, or at least about 50 wt %.

Embodiment 23

The method of any of Embodiments 17 to 21, wherein the cracked fraction is derived from a cracked feedstock where at least 15 wt % of the cracked feedstock is converted relative to a conversion temperature based on exposure to hydrogen-assisted cracking conditions, or at least about 20 wt %, or at least about 25 wt %, or at least about 50 wt %.

Embodiment 24

A method of characterizing a distillate boiling range fraction, comprising: determining a breakpoint for a first sample of a distillate fraction, the distillate fraction having an initial boiling point of at least about 284° F. (140° C.) and a final boiling point of about 572° F. (300° C.) or less, the distillate fraction being derived from a pre-refined crude oil, a cracked fraction, or a combination thereof, the determined breakpoint being greater than about 265° C.; heating a second sample of the distillate fraction in a vessel of a quartz crystal microbalance apparatus to an aging temperature for an aging period, the quartz crystal microbalance apparatus comprising a quartz crystal, the quartz crystal being disposed in the second sample during the heating; measuring a baseline frequency and an aged frequency of the quartz crystal, the aged frequency being measured after maintaining the second sample of the distillate fraction at the aging temperature for an aging period, the baseline frequency being measured prior to maintaining the second sample of the distillate fraction at the aging temperature for the aging period, a difference between the baseline frequency and the aged frequency for the second sample being greater than or equal to a threshold frequency difference value; blending a portion of the distillate fraction derived from the first pre-refined crude oil with a portion of a mineral distillate fraction to form a blended distillate fraction; and measuring a baseline frequency and an aged frequency for a sample derived from the blended distillate fraction using a quartz crystal microbalance apparatus, the aged frequency being measured after maintaining the sample derived from the blended distillate fraction at the aging temperature for the aging period, a difference between the baseline frequency and the aged frequency for the sample derived from the blended distillate fraction being less than the threshold frequency difference value.

Embodiment 25

The method of Embodiment 24, wherein measuring a baseline frequency and an aged frequency for the sample derived from the blended distillate fraction comprises measuring a baseline frequency and an aged frequency for a hydroprocessed sample derived from the blended distillate fraction.

Embodiment 26

The method of any of Embodiments 24 or 25, wherein the pre-refined crude oil, the cracked fraction, or the combination thereof comprises at least about 5 vol % of molecules formed during cracking or conversion in a hydrogen-limited environment, or at least about 10 vol %, or at least about 25 vol %, or at least about 50 vol %.

Embodiment 27

The method of any Embodiments 24 to 26, wherein the cracked fraction is derived from a cracked feedstock where at least 5 wt % of the cracked feedstock is converted relative to a conversion temperature based on exposure to hydrogen-limited cracking conditions, or at least about 110 wt %, or at least about 15 wt %, or at least about 25 wt %, or at least about 50 wt %.

Embodiment 28

The method of any of Embodiments 24 to 26, wherein the cracked fraction is derived from a cracked feedstock where at least 15 wt % of the cracked feedstock is converted relative to a conversion temperature based on exposure to hydrogen-assisted cracking conditions, or at least about 20 wt %, or at least about 25 wt %, or at least about 50 wt %.

Embodiment 29

The method of any of Embodiments 24 to 28, wherein a breakpoint of the blended sample is at least about 265° C., or at least about 275° C.

Embodiment 30

The method of any of Embodiments 17 to 29, wherein the aging temperature is about 40° C. to about 100° C., or about 45° C. to about 90° C., and the aging period is about 5 hours to about 24 hours, or about 8 hours to about 24 hours.

Embodiment 31

The method of any of Embodiments 17 to 30, wherein the first sampling period is about 5 minutes to about 24 hours.

Embodiment 32

The method of any of Embodiments 17 to 21, wherein measuring the baseline frequency comprises: sampling a frequency of the quartz crystal a plurality of times during at least a portion of the first sampling period; and determining the baseline frequency based on an average of at least a portion of the sampled frequency values from the at least a portion of the first sampling period.

Embodiment 33

The method of Embodiment 32, wherein measuring the aged frequency comprises: sampling a frequency of the quartz crystal a plurality of times during at least a portion of the second sampling period; and determining the aged frequency based on an average of at least a portion of the sampled frequency values from the at least a portion of the second sampling period.

Embodiment 34

The method of any of Embodiments 17 to 33, wherein the baseline temperature is about 25° C. to about 45° C., or about 27° C. to about 40° C., or at least about 30° C., or about 35° C. or less.

Embodiment 35

The method of any of Embodiments 17 to 34, wherein the threshold frequency difference value is about 40 Hz.

Additional Examples

Figure 9:
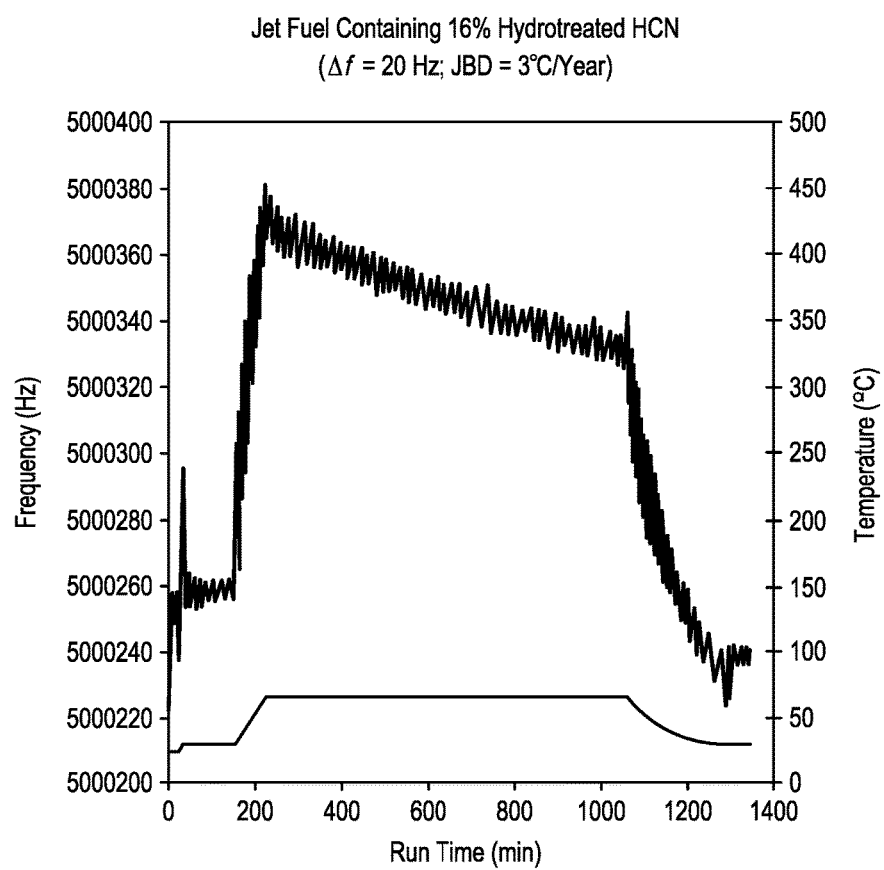
FIG. 9 shows frequency values for a sample containing a portion of hydrotreated heavy catalytic naphtha characterized in a quartz crystal microbalance apparatus and the corresponding temperature profile used for the characterization.
Figure 10:
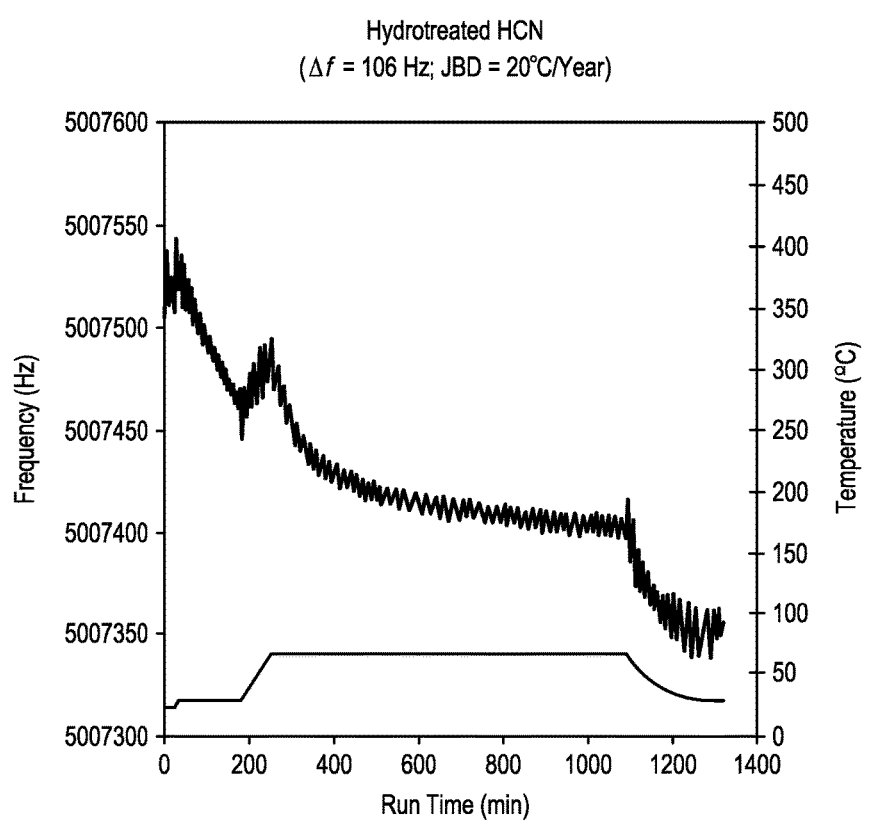
FIG. 10 shows frequency values for a sample containing a hydrotreated heavy catalytic naphtha characterized in a quartz crystal microbalance apparatus and the corresponding temperature profile used for the characterization.

FIGS. 9 and 10 show additional examples of results from using a quartz crystal microbalance apparatus to characterize sampled based on feedstocks containing at least a portion of cracked feed. The samples in FIGS. 9 and 10 were characterized according to the methods described herein for the characterization of samples. The temperature profile used for the characterizations in FIGS. 9 and 10 is included in the each of the figures.

In the example shown in FIG. 9, the feedstock contained 16 wt % of a hydrotreated heavy catalytic naphtha fraction. The remaining portion of the feedstock corresponded to a fraction derived from a virgin and/or hydrotreated (non-cracked) crude. For the results shown in FIG. 9, the sample tested in the QCM apparatus corresponded to a sample that was also tested by a conventional breakpoint testing method. The sample characterized in FIG. 9 had a JFTOT™ breakpoint degradation value of 3° C. per year, which is below the 10° C. threshold that corresponds to being fit for purpose for use as a jet fuel. As shown in FIG. 9, the sample has a frequency change of about 20 Hz, which is below the 39 Hz threshold for a sample tested according to the method used.

FIG. 10 shows results from characterization of a feedstock containing only a hydrotreated heavy catalytic naphtha fraction. For the results shown in FIG. 10, the sample tested in the QCM apparatus corresponded to a sample that was also tested by a conventional breakpoint testing method. The sample characterized in FIG. 10 had a JFTOT™ breakpoint degradation value of 20° C. per year, which is greater than the 10° C. per year threshold that corresponds to being fit for purpose for use as a jet fuel. As shown in FIG. 10, the sample has a frequency change of about 106 Hz, which is greater the 40 Hz threshold for a sample tested according to the method used. As shown in FIGS. 9 and 10, the methods described herein for use of a QCM apparatus are suitable for characterization of potential jet fuel fractions as satisfying the fit for purpose threshold related to JFTOT™ breakpoint degradation.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

What is claimed is:

1. A method of characterizing a kerosene boiling range sample, comprising:
    disposing a quartz crystal in a vessel containing a kerosene boiling range sample;
    heating the kerosene boiling range sample to a baseline temperature;
    measuring a frequency of the quartz crystal at the baseline temperature during a first sampling period to obtain a baseline frequency;
    heating the kerosene boiling range sample to an aging temperature and maintaining the sample at the aging temperature for an aging period;
    returning the kerosene boiling range sample to the baseline temperature; and
    measuring the frequency of the quartz crystal at the baseline temperature during a second sampling period to obtain an aged frequency, a difference between the baseline frequency and the aged frequency being indicative of a stability of the kerosene boiling range sample.

2. The method of claim 1, wherein the kerosene boiling range sample has a boiling range of about 140° C. to about 300° C.

3. The method of claim 1, wherein the baseline temperature is about 25° C. to about 45° C.

4. The method of claim 1, wherein the aging temperature is about 40° C. to about 100° C.

5. The method of claim 1, wherein the aging period is about 5 hours to about 24 hours.

6. The method of claim 1, wherein the first sampling period is about 5 minutes to about 24 hours.

7. The method of claim 1, wherein measuring the baseline frequency comprises: sampling a frequency of the quartz crystal a plurality of times during at least a portion of the first sampling period; and determining the baseline frequency based on an average of at least a portion of the sampled frequency values from the at least a portion of the first sampling period.

8. The method of claim 7, wherein measuring the aged frequency comprises: sampling a frequency of the quartz crystal a plurality of times during at least a portion of the second sampling period; and determining the aged frequency based on an average of at least a portion of the sampled frequency values from the at least a portion of the first sampling period.

9. The method of claim 8, wherein a time corresponding to the at least a portion of the first sampling period is the same as a time corresponding to the at least a portion of the second sampling period.

10. The method of claim 1, wherein the kerosene boiling range sample comprises a portion derived from a pre-refined crude oil, a portion derived from a cracked fraction, or a combination thereof.

11. The method of claim 10, wherein the portion derived from the pre-refined crude oil, the portion derived from the cracked fraction, or the combination thereof comprises at least about 10 vol % of molecules formed during cracking or conversion in a hydrogen-limited environment.

12. The method of claim 10, wherein the cracked fraction is derived from a cracked feedstock where at least about 10 wt % of the cracked feedstock is converted relative to a conversion temperature based on exposure to hydrogen-limited cracking conditions.

13. The method of claim 10, wherein the cracked fraction is derived from a cracked feedstock where at least about 20 wt % of the cracked feedstock is converted relative to a conversion temperature based on exposure to hydrogen-assisted cracking conditions.

14. The method of claim 1, further comprising determining a breakpoint for a second kerosene boiling range sample, the kerosene boiling range sample and the second kerosene boiling range sample being derived from the same source, the breakpoint for the second kerosene boiling range sample being at least about 265° C.

15. The method of claim 14, wherein the breakpoint for the second kerosene boiling range sample is at least about 275° C.

16. The method of claim 14, wherein the kerosene boiling range sample and the second kerosene boiling range sample are formed by obtaining a portion of a distillate fraction; and splitting the portion of the distillate fraction to form at least the kerosene boiling range sample and the second kerosene boiling range sample.

17. The method of claim 1, wherein the difference between the baseline frequency and the aged frequency is about 39 Hz or less.

18. A method of characterizing a distillate fraction, comprising:
    determining a breakpoint for a first sample of a distillate fraction, the distillate fraction having an initial boiling point of at least about 284° F. (140° C.) and a final boiling point of about 572° F. (300° C.) or less, at least a portion of the distillate fraction being derived from a first pre-refined crude oil, the determined breakpoint being greater than about 265° C.;
    heating a second sample of the distillate fraction in a vessel of a quartz crystal microbalance apparatus to an aging temperature, the aging temperature being from about 40° C. to about 90° C., the quartz crystal microbalance apparatus comprising a quartz crystal, the quartz crystal being disposed in the second sample during the heating; and
    measuring a baseline frequency and an aged frequency of the quartz crystal, the aged frequency being measured after maintaining the second sample of the distillate fraction at the aging temperature for an aging period, the baseline frequency being measured prior to maintaining the second sample of the distillate fraction at the aging temperature for the aging period, the aging period being from about 5 hours to about 24 hours,
    wherein a difference between the baseline frequency and the aged frequency is indicative of a stability of the distillate fraction.

19. The method of claim 18, wherein the baseline frequency and the aged frequency are measured at a baseline temperature, the baseline temperature being less than the aging temperature.

20. The method of claim 18, wherein the difference between the baseline frequency and the aged frequency is about 39 Hz or less.

* * * * *